United States Patent [19]

Kikuchi

[11] Patent Number: 5,045,935
[45] Date of Patent: Sep. 3, 1991

[54] ELECTRONIC ENDOSCOPE SYSTEM INCLUDING IMAGE PROCESSING UNIT WITH PHOTOGRAPHING UNIT

[75] Inventor: Katsuya Kikuchi, Tochigi, Japan
[73] Assignee: Kabushiki Kaisha Toshiba, Kawasaki, Japan
[21] Appl. No.: 506,244
[22] Filed: Apr. 9, 1990
[30] Foreign Application Priority Data
  Apr. 12, 1989 [JP] Japan .................................. 1-90570
[51] Int. Cl.⁵ .......................... H04N 7/18; A61B 1/04
[52] U.S. Cl. .......................................... 358/98; 128/6
[58] Field of Search .............................. 128/6; 358/98

[56] References Cited
U.S. PATENT DOCUMENTS

| | | | |
|---|---|---|---|
| 4,625,714 | 12/1986 | Toyota et al. | 128/6 |
| 4,699,125 | 10/1987 | Komatsu | 358/98 X |
| 4,712,133 | 12/1987 | Kikuchi | 358/98 |
| 4,914,512 | 4/1990 | Sekiguchi | 358/98 |
| 4,920,413 | 4/1990 | Nakamura et al. | 128/6 X |
| 4,947,245 | 8/1990 | Ogawa et al. | 358/98 |

Primary Examiner—Kenneth A. Wieder
Assistant Examiner—Glenn W. Brown
Attorney, Agent, or Firm—Foley & Lardner

[57] ABSTRACT

In an electronic endoscope system, an endoscopically-processed endoscopic image such as a color-enhanced endoscopic image is photographed with a simple operation. The electronic endoscope system comprises: an endoscopic image producing unit for producing an endoscopic image signal of an object under medical examination as original endoscopic image data; an endoscopic image processing unit for processing the original endoscopic image data so as to obtain endoscopically-processed image data; a photographing unit for selectively photographing the original endoscopic image data and the endoscopically-processed image data; an image confirming unit for selectively receiving the original endoscopic image data and the endoscopically-processed image data so as to confirm a content of the received image data; and, an image data transferring unit for transferring the original endoscopic image data and the endoscopically-processed image data simultaneously to at least both the photographing unit and image confirming unit in response to an instruction signal. Then, the transferred image data is photographed by the photographing means while the content thereof is confirmed by the image confirming unit.

12 Claims, 5 Drawing Sheets

ELECTRONIC ENDOSCOPE SYSTEM INCLUDING IMAGE PROCESSING UNIT WITH PHOTOGRAPHING UNIT

BACKGROUND OF THE INVENTION

1. Field of the Invention

The present invention generally relates to an electronic endoscope system capable of displaying various processed images, e.g., a hemoglobin-concentration-distributed image. More specifically, the present invention is directed to an electronic endoscope system capable of photographing such various processed images with an easy operation.

2. Description of the Related Art

Recently, remarkable progress has been made in electronic endoscope systems which can not only display and record as a photograph an original endoscopic image of an object under medical examination, e.g., an interior of a stomach, but also can display a specifically-processed image thereof in a real time mode, a hemoglobin-concentration-distributed image, and an infrared image.

However, the above-described conventional endoscope system has the following problems. That is, when both the original endoscopic image of the object under medical examination and specifically-processed endoscopic images such as a hemoglobin-concentration-distributed image are displayed on a color TV monitor, or photographed for recording purposes, after the desired image has been selected by switching the images so as to be displayed on the color TV monitor, an additional operation for photographing the image displayed on this color TV monitor is required. As a consequence, various cumbersome operations are necessarily required for photographing such specifically-processed endoscopic images while a medical examination is carried out with employment of the conventional electronic endoscope system. Furthermore, since such cumbersome operations have been performed, the originally required medical examinations per se are delayed.

The present invention has been made in an attempt to solve the above-described problems of the conventional electronic endoscope systems, and therefore has an object to provide an electronic endoscope system capable of photographing a plurality of specifically-processed endoscopic images without repeatedly executing cumbersome operations.

SUMMARY OF THE INVENTION

The above-described object and other features of the present invention may be achieved by providing an electronic endoscope system comprising:

endoscopic image producing means (10:11:12) for producing an endoscopic image signal of an object under medical examination as original endoscopic image data;

endoscopic image processing means (9) for processing said original endoscopic image data so as to obtain endoscopically-processed image data;

photographing means (2) for selectively photographing said original endoscopic image data and said endoscopically-processed image data;

image confirming means (1:13:58) for selectively receiving said original endoscopic image data and said endoscopically-processed image data so as to confirm a content of said received image data; and, image data transferring means (3:15) for transferring said original endoscopic image data and said endoscopically-processed image data simultaneously to at least both said photographing means (2) and image confirming means (1:13:58) in response to an instruction signal, whereby said transferred image data is photographed by said photographing means (2) while the content thereof is confirmed by the image confirming means (1:13:58).

BRIEF DESCRIPTION OF THE DRAWINGS

The above-described aspects and other objects of the invention will be explained more in detail in the following description, in conjunction with the accompanying drawings, in which.

DETAILED DESCRIPTION OF THE PREFERRED EMBODIMENTS

Construction of First Endoscope System

Figure 1:
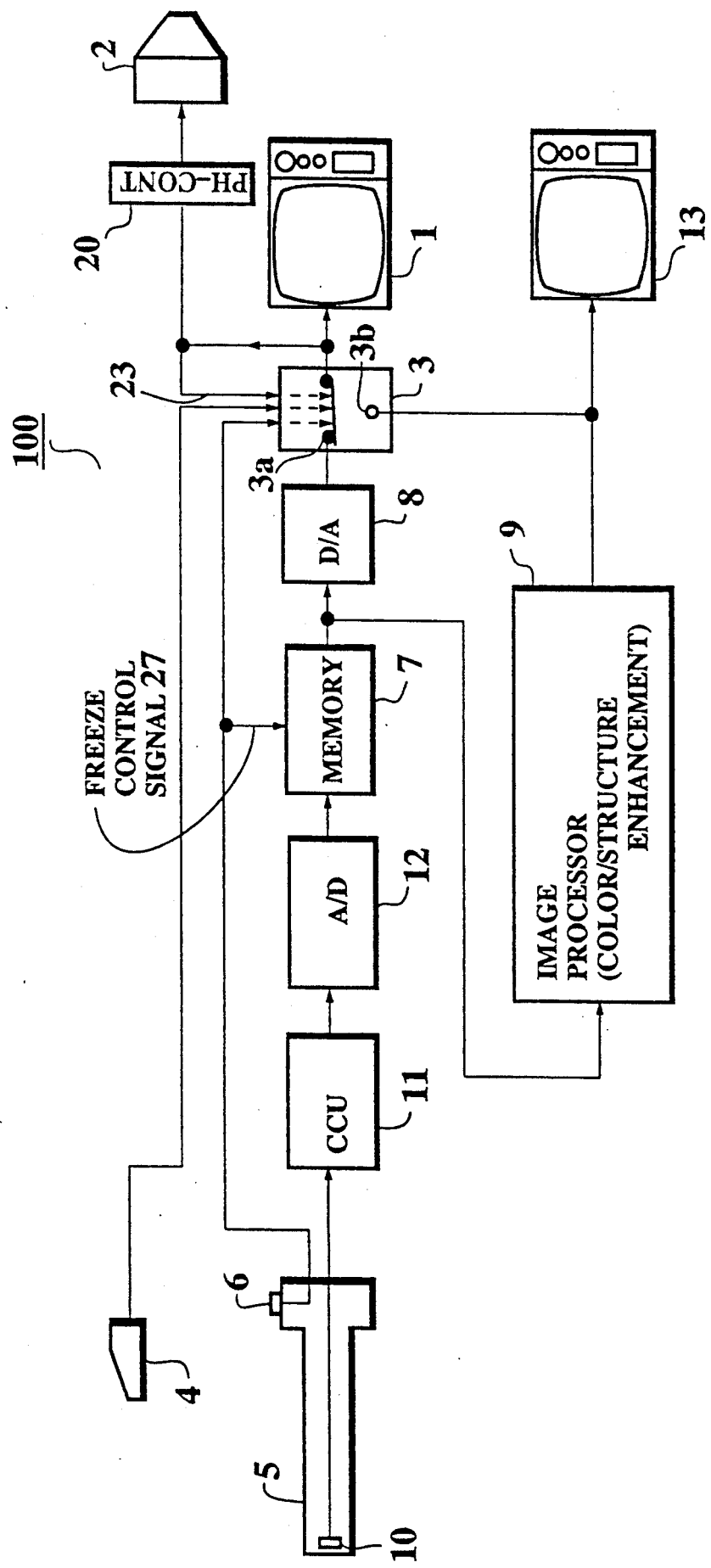
FIG. 1 is a schematic block diagram of an electronic endoscope system 100 including a selector 3, according to a first preferred embodiment of the present invention.

In FIG. 1, there is shown a construction of an electronic endoscope system 100 according to a first preferred embodiment of the present invention.

The first electronic endoscope system 100 comprises a main TV (television) monitor 1 for displaying an endoscopic image, so-called an original endoscopic image of an object (not shown in detail) under medical examination, i.e., an interior of a stomach in a real time mode; a photographing unit 2 for photographing an image-processed original endoscopic image, for instance, a structure-enhanced image or a functional image; a selector 3 selectively connected to the main TV monitor 1 and photographing unit 2, and a photographing control unit 20 interposed between the photographing unit 2 and selector 3.

This first endoscope system 100 further includes a foot switch 4; an endoscopic scope 5 having a solid-state image sensor, e.g., CCD (charge-coupled device) 10 at one distal end and also a copy switch 6 at the other distal end; a series circuit including a camera control unit 11, an analog-to-digital converter 12, an image memory 7 and a digital-to-analog converter 8, and interposed between the above-described scope 5 and selector 3;

An image processing unit 9 for specifically-processing the original endoscopic image stored in the image memory 7 so as to obtain an image-processed original endoscopic image, e.g., a structure-enhanced image;

and a sub TV monitor 13 for displaying the image-processed image.

More specifically, the selector 3 is selectively connected further to the D/A converter 8 and image processing unit 9. This selector 3 functions as an image data transfer means, and selects a proper contact 3a or 3b in response to a manual switching operation by the foot switch 4. Similarly, this selector 3 automatically switches both the first contact 3a and second contact 3b in response to the switching operation by the copy switch 6. As a result, in the normal condition, the image data (i.e., original endoscopic image of the object) which have been stored in the image memory 7, are sequentially read out and then D/A converted into the corresponding original endoscopic analog image signals by the D/A converter 8, which are successively supplied to the first contact 3a of the selector 3. When either the foot switch 4 or copy switch 6 is operated, the selector contact 3b is selected to be connected to the image processing unit 9, so that the image-processed original image data are sequentially supplied to this contact 3b.

OPERATIONS OF FIRST ENDOSCOPE SYSTEM

When the object under medical examination (not shown in detail) is illuminated by the light guide (not shown in detail) of the endoscopic scope 5, the CCD image sensor 10 positioned at one distal end of the scope 5 senses the image of this object to produce an image signal thereof by way of the known photo-electronic conversion technique. The image signal is further converted into a proper type of video signal by the camera control unit 11, which is A/D-converted into a digital image signal by the A/D converter 12 and thereafter stored as original endoscopic image data into the image memory 7.

In the normal condition, the original endoscopic image data stored in the image memory are sequentially read out and D/A-converted into the analog image signals which will be then supplied via the first contact 3a of the selector 3 to the main TV monitor 1, since the first contact 3a is selected in response to the switching operation of the foot switch 4. Thus, the original endoscopic image is displayed on this main TV monitor 1 in a real time mode, so that an operator can observe this real-time original image displayed on the main TV monitor 1 during the medical examination On the other hand, the original endoscopic image data read out from the image memory 7 are sequentially supplied to the image processing unit 9 so as to be processed therein by the color enhancement and/or structure enhancement in a real time mode. Accordingly, the resultant image-processed endoscopic image can be displayed on the sub TV monitor 13. While such an image-processed endoscopic image, e.g., color-enhanced image is being displayed on the main TV monitor 1 when the foot switch 4 is operated to select the second contact 3b, this color-enhanced image may be photographed by the photographing unit 2 (will be discussed later).

PHOTOGRAPHING OPERATION

While the endoscopic examination of the object under medical inspection is carried out and the desired original endoscopic image displayed on the main TV monitor 1 is observed by the operator, this desired original endoscopic image is designated by depressing the copy switch 6, so that this original image is electronically frozen in the image memory 7 in response to a freeze control signal 27 produced by the copy switch 6. Then, the frozen image data of the image memory 7 is D/A-converted into a corresponding analog frozen image signal. The analog frozen image signal is then supplied via the first contact 3a of the selector 3 to both the main TV monitor 1 and the photographing unit 2 through the photographing control unit 20. As a result, the frozen original endoscopic image is displayed on the main TV monitor 1 and simultaneously photographed by the photographing unit 2 under the control of the photographing control unit 20.

When the photographing operation of the frozen original image of the object under medical examination is accomplished, it is detected by the photographing control unit 20. Thus, the photographing control unit 20 transfers a selector control signal 23 to the selector 3 so as to automatically change the first contact 3a into the second contact 3b. As a result, the specifically-processed image signal (e.g., color-enhanced image signal) derived from the image processor 9 is furnished to both the main TV monitor 1 and photographing unit 2 via the photographing control unit 20. Under these conditions, a frozen image of the specifically-processed endoscopic image corresponding to the original endoscopic image is selected and displayed on the main TV monitor 1 and simultaneously photographed by the photographing unit 2 under the control of the photographing control unit 20.

With the above-described series of the photographing operations, two different types of frozen endoscopic images, i.e., frozen original image and frozen specifically-processed image (e.g., color-enhanced image) are photographed by the photographing unit 2.

It should be noted that since the above-described image freezing function is realized by the known operations of the image memory, no further explanation thereof is made in the following description. In case that the second contact 3b of the selector 3 has been selected during the freezing operation, the specifically-processed image corresponding to the original endoscopic image is displayed on the main TV monitor 1, and simultaneously photographed by the photographing unit 2 under the control of the photographing control unit 20. Subsequently, when the copy switch 6 is depressed, the first contact 3a of the selector 3 is selected. As a consequence, the frozen image of the original endoscopic image derived from the image memory 7 is displayed on the main TV monitor 1 and photographed by the photographing unit 2 under the control of the photographing control unit 20 at the same time. Anyway, the photographing unit 2 may photograph both the frozen original endoscopic image and the frozen specifically-processed image corresponding to this original endoscopic image according to the first electronic endoscope system 100.

CONSTRUCTION OF SECOND ELECTRONIC ENDOSCOPE SYSTEM

Figure 2:
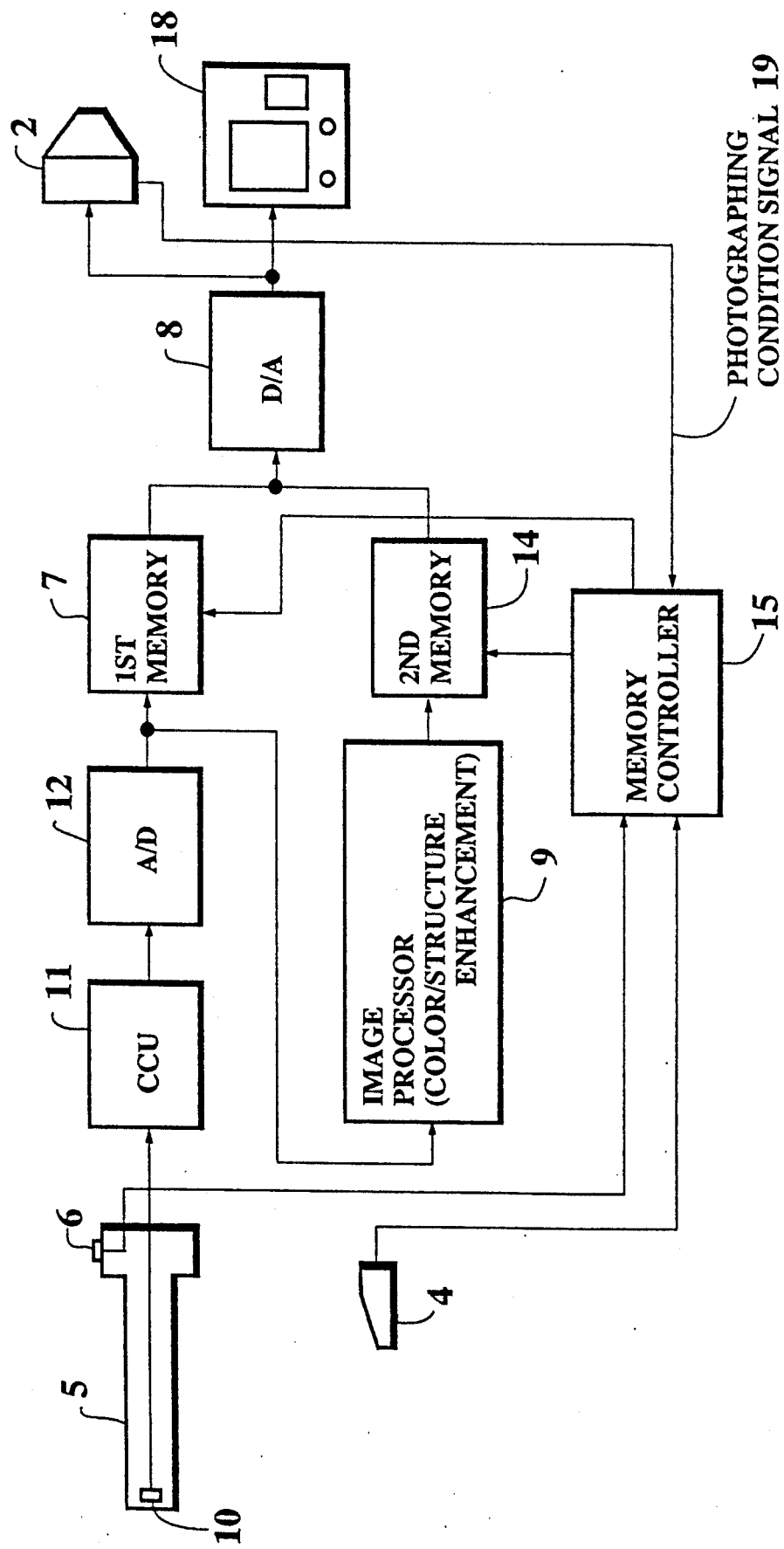
FIG. 2 is a schematic block diagram of an electronic endoscope system 200 including a memory controller 15, according to a second preferred embodiment of the present invention.

Referring now to FIG. 2, an electronic endoscope system 200 including a memory controller 15, according to a second preferred embodiment, will now be described.

As apparent from FIG. 2, the major circuit of the second electronic endoscope system 200 is similar to that of the above-described first electronic endoscope system 100. Therefore, only different circuit portions will now be described. That is, a second image memory 14 is employed so as to store the specifically-processed image data derived from the image processing unit 9. Accordingly, both the original endoscopic image data stored in the first image memory 7 and the specifically-processed image data stored in the second image memory 14 are selectively supplied to the D/A converter 8. This D/A converter 8 is connected to both a dual-display mode type TV monitor 18, and the photographing unit 2. Furthermore, a memory controller 15 is newly employed which receives the switching operation signals from the foot switch 4 and copy switch 6, and also the photographing condition signal from the photographing unit 2. The memory controller 15 controls both the first and second image memories 7 and 14 for the read and write operations of the endoscopic image data.

FUNCTION/ARRANGEMENT OF MEMORY CONTROLLER

This memory controller 15 plays an important feature in the second electronic endoscope system 200, and has the similar function to the above-described image data transfer control means, i.e., the selector 3 of the first electronic endoscope system 100. In response to the instructions from the foot switch 4, a selection of read/write operations for the first and second image memories 7 and 14 can be executed by this memory controller 15. Also, in response to the instructions of the copy switch 6 of the endoscopic scope 5, both an automatic selection of read/write operations and image freezing operations for the first and second image memories 7 and 14 can be performed under the control of the memory controller 15.

Figure 3:
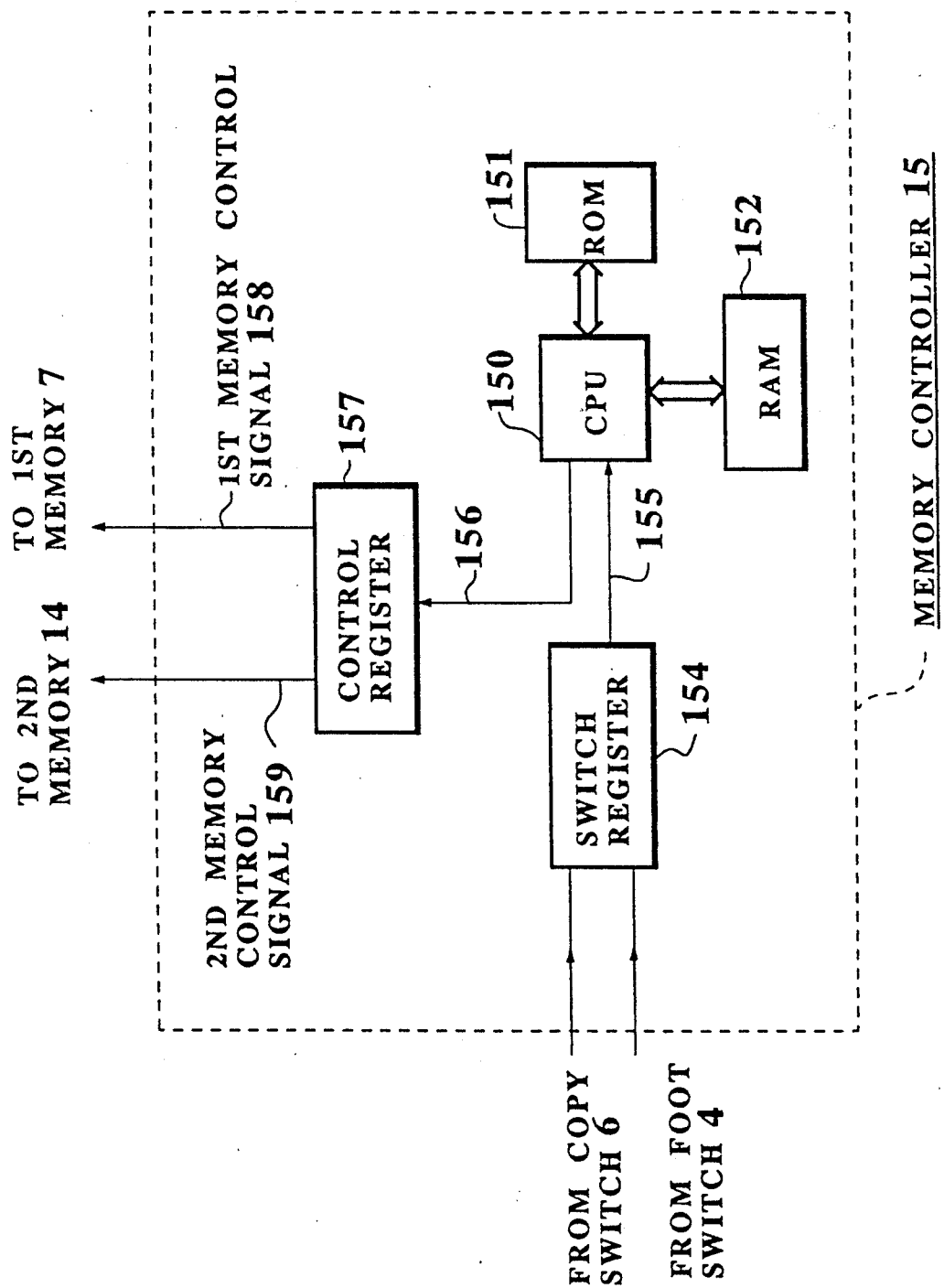
FIG. 3 is a circuit block diagram of the memory controller shown in FIG. 2.

In FIG. 3, there is shown an internal circuit of the memory controller 15.

In the memory controller 15, a central processing unit (referred to "CPU") 150 is employed so as to control an overall system. When a power supply switch (not shown in detail) is turned ON, system control software which has been previously stored into ROM 151 is read out from this ROM 151 and written into RAM 152 under the control of CPU 150. Thereafter, when one of the endoscopic processing switches, e.g., the copy switch 6, is operated, a switch register 154 registers such a state that the copy switch 6 is manipulated, and then outputs a copy switch manipulation signal 155 to CPU 150. In response to this copy switch manipulation signal 155, CPU 150 sequentially writes a register control signal 156 into a control register 157. In response to this register control signal 156, the control register 157 produces, for instance, a first memory control signal 158 in accordance with the system control software previously written into ROM 151, whereby the real time endoscopic image data are read out from the first memory 7 for the copying process purpose by the photographing unit 2.

DUAL DISPLAY MODES

During the endoscopic operations of the second electronic endoscope system 200, both the original endoscopic image data of the first image memory 7 and the specifically-processed image data of the second image memory 14 are read out therefrom under the control of the memory controller 15, and thereafter D/A-converted by the D/A converter 8. Both the converted analog image signals are furnished to the dual-display mode type monitor 18.

Figure 4A:
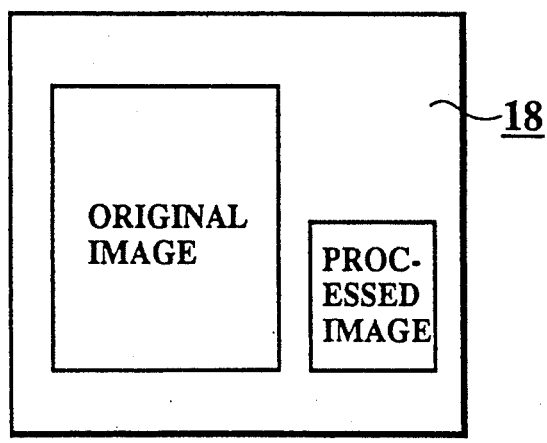
FIG. 4A and 4B illustrate monitor displays of dual-display mode type monitor employed in the second electronic endoscope system 200 shown in FIG. 2.

Thus, the original endoscopic image outputted from the first image memory 7 is displayed on the dual-display mode type monitor 18, as represented in FIG. 4A (i.e., left-sided image) and simultaneously the specifically-processed endoscopic image outputted from the second image memory 14 is displayed on this monitor 18, as represented in FIG. 4A (i.e., right-sided image).

Figure 4B:
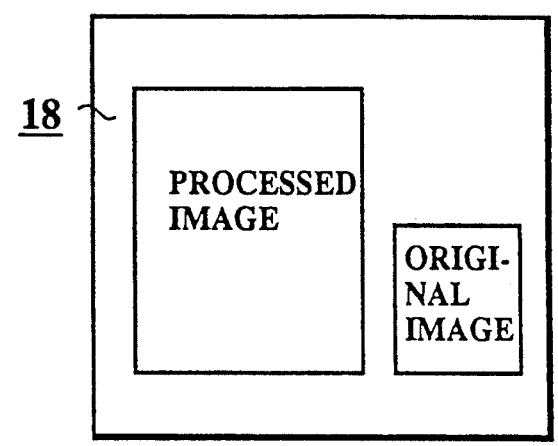

That is to say, the original endoscopic image is displayed on the main screen of the dual-display mode type monitor 18, whereas the specifically-processed image is displayed on the sub-screen thereof as represented in FIG. 4A. To the contrary, the specifically-processed image is displayed on the main screen of this dual-display mode type monitor 18, whereas the original endoscopic image is displayed on the sub-screen thereof as represented in FIG. 4B. The selection of such display conditions shown in FIGS. 4A and 4B is realized by controlling the read/wrote operations of the first and second image memories 7 and 14 under the control of the memory controller 15 in response to the switching operations of the foot switch 4.

PHOTOGRAPHING OPERATIONS

Figure 5A:
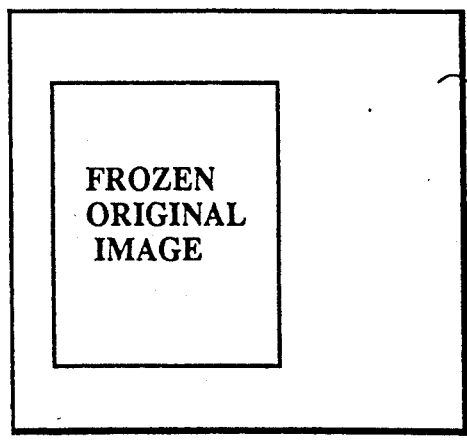
FIG. 5A and 5B illustrate frozen images displayed on the monitor employed in the second electronic endoscope system 200 shown in FIG. 2; and, FIG. 6 is a schematic block diagram of an electronic endoscope system 300 including a Hb-processor 50, according to a third preferred embodiment of the present invention.

Under these circumstances, when the desired image is photographed in the second electronic endoscope system 200, the photographing operations can be performed by depressing the copy switch 6 mounted on the endoscopic scope 5. That is, when the copy switch 6 is depressed, only the frozen original endoscopic image of the object under medical examination is displayed under the control of the memory controller 15 on the dual-display mode type monitor 18 as represented in FIG. 5A. At the same time, this frozen original image is photographed by the photographing unit 2.

Figure 5B:
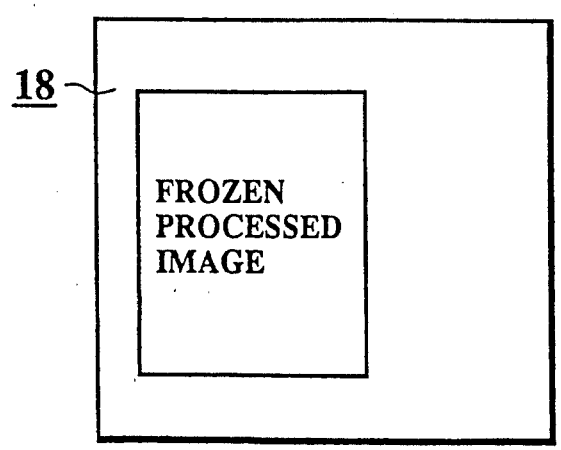

Immediately after the above-described photographing operation of the frozen original image, a photographing condition signal 19 is supplied from the photographing unit 2 to the memory controller 15. Accordingly, only the frozen specifically-processed image is displayed on this dual-display mode type monitor 18 as represented in FIG. 5B, and simultaneously photographed by the photographing unit 2.

THIRD ELECTRONIC ENDOSCOPE SYSTEM FOR HEMOGLOBIN CONCENTRATION DISTRIBUTED IMAGE

Figure 6:
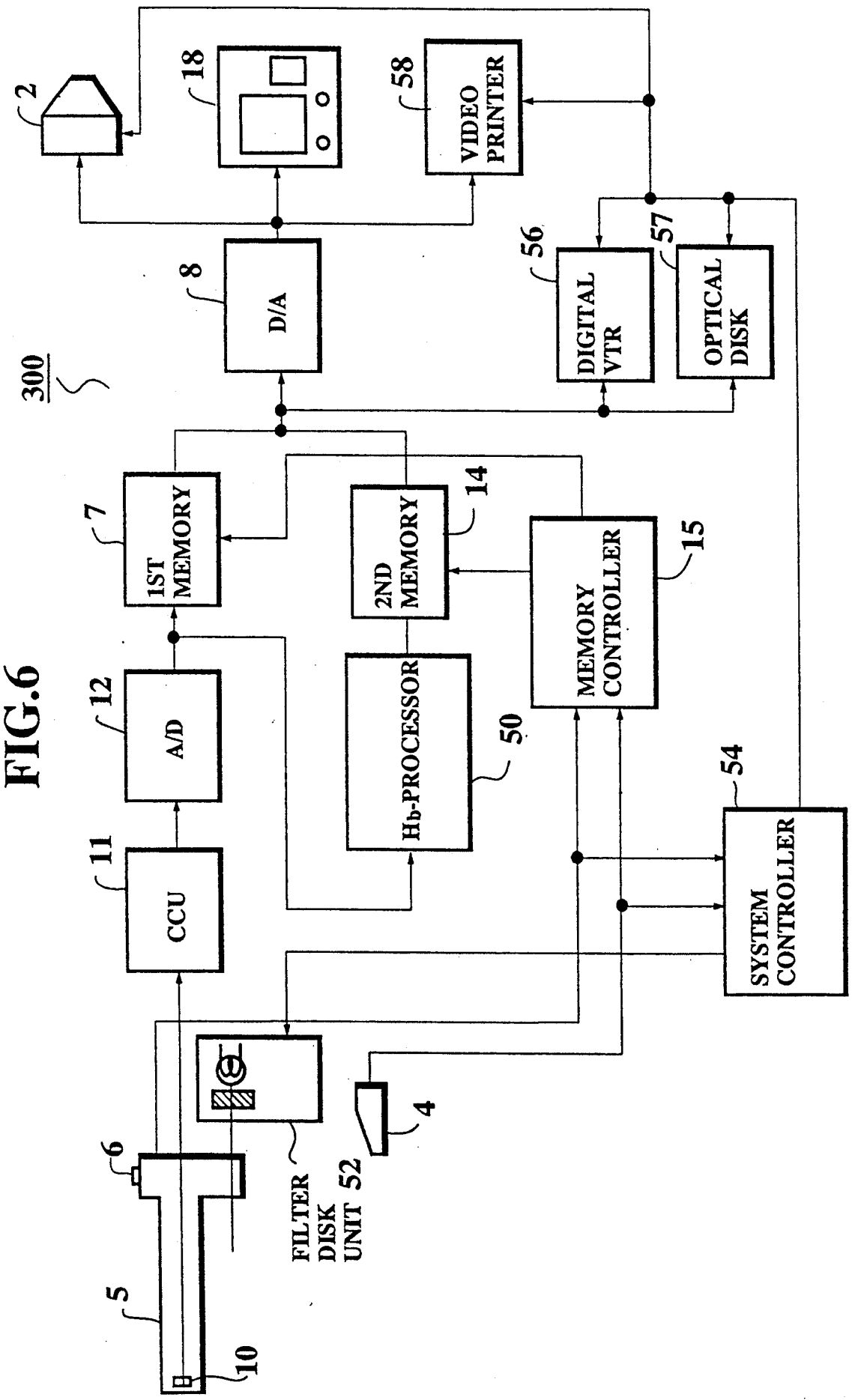

As previously described in detail, in the first and second electronic endoscope systems 100 and 200, the image processing unit 9 performs the color enhancement (e.g., saturation enhancement) and/or structure enhancement on the original endoscopic image. To the contrary, a different image-processing operation may be carried out in an electronic endoscope system 300 according to a third preferred embodiment of the present invention, as represented in FIG. 6. That is, a hemoglobin concentration processing unit 50 is newly employed in conjunction with a filter disk unit 52 and a system controller 54. Furthermore, a digital VTR (video tape recorder) 56, an optical disk unit 57 and a video printer 58. Since other circuits of the third electronic endoscope system 300 are similar to those of the second electronic endoscope system 200, no further explanation thereof is made in the following description.

Accordingly, only a specific feature of the third electronic endoscope system 300 will now be described. When the proper filters (not shown in detail) of the filter disk unit 52 are selected under the control of the system controller 54, endoscopic image data having a preselected light absorbance characteristic determined by the selected filters are successively produced in the hemoglobin concentration processing unit 50 and thereafter sequentially stored in the second memory 14. Under the control of the memory controller 15, these specifically-processed image data are sequentially read out from the second memory 14 so as to be furnished to the D/A converter 8, digital VTR 56 and optical disk unit 57. Thus, the hemoglobin-concentration-processed (-distributed) image data (frozen image data) may be recorded on the digital VTR 56 and/or optical disk unit 57. On the other hand, the D/A-converted hemoglobin concentration image signals are supplied to the dual-display mode type monitor 18, photographing unit 2 and video printer 58. When the copy switch 6 is operated, these frozen hemoglobin concentration image signals may be automatically and sequentially photographed by the photographing unit 2, and also may be printed out by the analog video printer 58.

As apparent from the foregoing, the present invention is not limited to the above-described typical preferred embodiments 100, 200 and 300, but may be readily modified. For instance, an infrared image processing unit may be employed, instead of the hemoglobin concentration processing unit.

As previously described in detail, in the electronic endoscope systems according to the present invention, there are particular advantages that since both the original endoscope image and various specifically-processed images corresponding thereto can be automatically photographed by simply designating the desirable original image only once, e.g., by depressing the copy switch only one time, the work loads loaded on an operator to photograph a plurality of endoscopic images can be considerably reduced, as compared with in the conventional electronic endoscope system.

What is claimed is:

1. An electronic endoscope system comprising:
   endoscopic image producing means for producing an endoscopic image signal of an object under medical examination as original endoscopic image data of said object;
   endoscopic image processing means for processing said original endoscopic image data so as to obtain endoscopically-processed image data;
   photographic means for successively photographing said original endoscopic image data and said endoscopically-processed image data;
   image confirming means for successively receiving said original endoscopic image data and said endoscopically-processed image data so as to confirm the contents of said original and endoscopically-processed image data; and,
   image data transferring means for simultaneously transferring said original endoscopic image data and said endoscopically-processed image data to at least both said photographing means and image confirming means in response to an instruction signal, whereby said original and endoscopically-processed image data simultaneously transferred to said image data confirming means are successively photographed by said photographing means while the contents thereof are confirmed by the image confirming means.

2. An electronic endoscope system as claimed in claim 1, wherein said image producing means includes:
   a solid-state image sensor positioned at one distal end of a scope, for photoelectric-converting an image of said object into said endoscopic image signal thereof;
   a camera control unit for converting said endoscopic image signal into an original endoscopic image signal; and,
   an analog-to-digital (A/D) converter for A/D-converting said original endoscopic image signal into the original endoscopic image data.

3. An electronic endoscope system as claimed in claim 1, wherein said endoscopic image processing means processes said original endoscopic image data so as to obtain hemoglobin-concentration-distributed image data, as the endoscopically-processed image data.

4. An electronic endoscope system as claimed in claim 1, wherein said endoscopic image processing means processes original endoscopic image data so as to obtain color-enhanced image data, as the endoscopically-processed image data.

5. An electronic endoscope system as claimed in claim 1, wherein said endoscopic image processing means processes original endoscopic image data so as to obtain structure-enhanced image data, as the endoscopically-processed image data.

6. An electronic endoscope system as claimed in claim 1, wherein said endoscopic image processing means processes said original endoscopic image data so as to obtain infrared image data, as the endoscopically-processed image data.

7. An electronic endoscope system as claimed in claim 1, wherein said image confirming means includes:
   a first television monitor for successively displaying said original endoscopic image of said object under medical examination in a real time mode and said endoscopically-processed endoscopic image thereof in a frozen image mode; and,
   a second television monitor for displaying said endoscopically processed endoscopic image in a real time mode.

8. An electronic endoscope system as claimed in claim 1, wherein said image confirming means includes:
   a monitor successively capable of displaying in a dual-display mode both an original endoscopic image of said object under medical examination in a real time mode and an endoscopically-processed endoscopic image thereof in a real time mode; and
   a video printer for printing out said original endoscopic image and endoscopically-processed endoscopic image.

9. An electronic endoscope system as claimed in claim 1, wherein said image data transferring means is a selector having first and second switchable contacts.

10. An electronic endoscope system as claimed in claim 1, wherein a first image memory is employed to store said original endoscopic image data derived from said endoscopic image producing means; a second image memory is employed to store said endoscopically-processed endoscopic image data derived from said endoscopic image processing means; and a memory controller is employed as said image data transferring means so as to control both said first and second image memories.

11. An electronic endoscope system as claimed in claim 10, wherein said memory controller 15 includes:
    a switch register for receiving said instruction signal to output a switch manipulation signal;
    a processing unit for processing said switch manipulation signal based upon a system control program to produce a register control signal; and,
    a control register for selectively producing a first memory control signal and a second control signal in response to said register control signal.

12. An electronic endoscope system as claimed in claim 1, wherein said instruction signal is produced from a selected one of a copy switch and a foot switch.

* * * * *